United States Patent [19]

Blaschke et al.

[11] Patent Number: 4,595,772
[45] Date of Patent: Jun. 17, 1986

[54] NOVEL WATER-SOLUBLE ANTIMONY COMPOUNDS AND THEIR PREPARATION

[75] Inventors: Marilyn W. Blaschke, Pearland; Richard F. Miller; John Link, both of Humble, all of Tex.

[73] Assignee: Atlantic Richfield Company, Los Angeles, Calif.

[21] Appl. No.: 672,558

[22] Filed: Nov. 19, 1984

[51] Int. Cl.$^4$ .............................................. C07F 9/90
[52] U.S. Cl. .................................... 556/77; 556/76
[58] Field of Search .................... 260/446; 556/76, 77

[56] References Cited

U.S. PATENT DOCUMENTS

| | | | |
|---|---|---|---|
| 3,728,367 | 4/1973 | Yates | 260/446 |
| 3,732,182 | 5/1973 | Chimura et al. | 260/446 X |
| 3,752,837 | 8/1973 | Okuto et al. | 260/446 |
| 3,764,378 | 10/1973 | Kemp | 260/446 X |
| 3,888,774 | 6/1975 | Kemp | 260/446 X |
| 4,010,104 | 3/1977 | Radlmann et al. | 260/446 X |
| 4,018,809 | 4/1977 | Radlmann et al. | 260/446 |

Primary Examiner—Helen M. S. Sneed
Attorney, Agent, or Firm—Coleman R. Reap

[57] ABSTRACT

Novel organic water-soluble antimony compounds are prepared by reacting an alkanolamine with a hydroxycarboxylic acid to form an intermediate product and then reacting the intermediate product with an antimony oxide. These compounds are useful for use as catalyst metal poison passivators.

9 Claims, No Drawings

NOVEL WATER-SOLUBLE ANTIMONY COMPOUNDS AND THEIR PREPARATION

FIELD OF THE INVENTION

The present invention relates to novel water-soluble antimony compounds which are useful as hydrocarbon cracking catalyst metal poison passivators and to the preparation of these novel water-soluble antimony compounds.

RELATED CASE

U.S. application Ser. No. 672,557, filed Nov. 19, 1984 relates to a method of passivating hydrocarbon catalyst metal poisons using water-soluble antimony compounds.

BACKGROUND OF THE INVENTION

Silica-containing or silica-alumina-containing materials are conventionally employed in the catalytic cracking of hydrocarbons for the production of gasoline, motor fuel, blending components and light distillates. Such materials are frequently associated with zeolitic substances. These zeolitic substances can be naturally occurring, or they can be produced by conventional ion exchange methods to provide metallic ions which improve the activity of the catalyst.

While the presence of certain metals in the catalyst can be beneficial, the presence of others is detrimental. It is well known that varying amounts of metals such as nickel, copper, cobalt, vanadium and iron cause deterioration of the cracking catalyst during the cracking process. In fact, some oils contain these metals in such a high concentration that they cannot be economically cracked into gasoline and other fuels. The metals accumulate on the cracking catalyst and cause increased hydrogen production and coke laydown on the cracking catalyst, thereby adversely affecting the yield of desired products.

It has heretofore been proposed that in hydrocarbon cracking processes those deleterious metals contained in the hydrocarbon feedstock can be passivated by treating the cracking catalyst with compounds containing antimony, tin, indium or bismuth (see U.S. Pat. Nos. 4,238,362, 4,279,735 and 4,257,919). Antimony compounds are particularly useful as passivating agents and use of a wide variety of both organic and inorganic antimony compounds have been proposed for that purpose (see U.S. Pat. Nos. 4,111,845 and 4,153,536). Other organic antimony compounds proposed are various antimony tricarboxylates. These antimony compounds, for the most part, have been used in the form of a hydrocarbon solution. Some antimony compounds, such as antimony trioxide, have been used in the form of aqueous slurries or emulsions. It would be advantageous to have water-soluble antimony compounds that would not introduce additional cracking catalyst poisons available for use as cracking catalyst poison passivators. Such compounds could be easily and conveniently injected into catalytic cracking units. Water-soluble antimony salts could be prepared by neutralizing antimony carboxylates with alkali or alkaline earth metal compounds, such as oxides or hydroxides, but the alkali or alkaline earth metal would itself act as a poison to the cracking catalyst, thus defeating the purpose of using the antimony compound.

It is an object of the invention to present novel organoantimony compounds. It is another object of the invention to present novel water-soluble organoantimony compounds. It is another object of the invention to present novel water-soluble antimony compounds which have utility as cracking catalyst metal poison passivators. It is another object of the invention to present a process for preparing water-soluble antimony carboxylates which are free of cracking catalyst poisons. These and other objects of the invention are supported in the following description and examples.

SUMMARY OF THE INVENTION

Novel antimony compounds have now been discovered which have good water-solubility and which can be easily and efficiently introduced into a hydrocarbon catalytic cracking unit. These novel compounds are antimony amino carboxylic acid salts which are prepared by the reaction of an alkanolamine with a hydroxycarboxylic acid and the subsequent reaction of the resulting product with antimony oxide.

DETAILED DESCRIPTION OF THE INVENTION

Considering the invention in more detail, the novel products are prepared by (a) reacting a mono-, di- or trifunctional alkanolamine with a hydroxycontaining saturated aliphatic acid, (b) reacting the product of (a) with an antimony oxide, and (c) recovering the antimony salt The alkanolamine has the structural formula

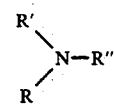

wherein R and R' may be identical or different and each may be hydrogen, a straight- or branch-chained alkyl group having 1 to 10 or more carbon atoms or a straight- or branch-chained alkanol group having 1 to 10 or more carbon atoms, and R" is a straight- or branch-chained alkanol having 1 to 10 or more carbon atoms.

When R, R' are alkyl groups they usually each have 1 to about 10 carbon atoms and preferably have 1 to about 6 carbon atoms and when they are alkanol groups they usually have 2 to 10 and preferably have 2 to 6 carbon atoms. R" usually has 2 to about 10 and preferably has 2 to about 6 carbon atoms. The total number of carbon atoms in R, R' and R" is 2 to about 12 carbon atoms and preferably 2 to about 8 carbon atoms.

Typical alkanolamines include unsubstituted and alkyl-substituted mono-, di- and trifunctional alkano lamines such as ethanolamine, propanolamine, hexanolamine, decanolamine, methylethanolamine, dimethylpropanolamine, ethyldecanolamine, diethanolamine, dipropanolamine, dihexanolamine, N-hydroxyethyl-N-hydroxypropylamine, N-hydroxybutyl-N-hydroxyloctylamine, N-methyldiethanolamine, triethanolamine, triisopropanolamine, N,N-bis(hydroxymethyl)-N-hydroxypropylamine, N,N-bis (hydroxyethyl)-N-hydroxyhexylamine, N-hydroxyethyl-N-hydroxymethyl-N-hydroxypropylamine, N-hydroxybutyl-N-hydroxyethyl-N-hydroxyhexylamine, etc.

Preferred alkanolamines are the lower alkanoamines, such as ethanolamine, propanolamine, butanolamine, diethanolamine, dipropanolamine, triethanolamine, tripropanolamine, N,N-dimethylethanolamine, N-methyldiethanolamine etc.

The hydroxycarboxylic acids usable in the invention are those saturated, straight or branched aliphatic hydroxycarboxylic acids which react with alkanolamines and antimony oxide to form water-soluble products. Preferred hydroxycarboxylic acids are those which have a hydroxyl group in the alpha position, i.e. attached to the carbon atom which is adjacent to the carboxyl group. The hydroxycarboxylic acid may have more than one carboxyl group and more than one hydroxyl group. In general, although higher hydroxycarboxylic acids may be used, the preferred hydroxycarboxylic acids are those having 2 to about 10 total carbon atoms, 1 to about 4 carboxyl groups and 1 to about 4 hydroxyl groups, because these are commercially available and are economical to use.

Typical suitable hydroxycarboxylic acids include monohydroxy-monocarboxylic acids, such as hydroxyacetic acid (glycolic acid), alpha-hydroxypropionic acid (lactic acid), alpha-hydroxybutyric acid, alpha-hydroxy-alpha methylpentanoic acid, etc.; monohydroxypolycarboxylic acids, such as hydroxymalonic acid, hydroxysuccinic acid (malic acid), 2 hydroxy-1,2,3-propanetricarboxylic acid (citric acid), etc.; polyhydroxy-monocarboxylic, acids such as 2,3-dihydroxypropionic acid, 2,5-dihydroxypentanoic acid, 2,3,4 trihydroxybutyric acid, 2,3,4,5,6-pentahydroxyhexanoic acid (gluconic acid), etc.; and polyhydroxypolycarboxylic acids, such as 2,3-dihydroxysuccinic acid (tartaric acid) 2,3,4 trihydroxyglutaric acid, etc. Preferred hydroxycarboxylic acids are the lower hydroxycarboxylic acids, such as tartaric acid, 2,4-dihydroxyglutaric acid, lactic acid, citric acid, etc.

The antimony oxide may be any oxide of antimony, however the preferred antimony oxides are antimony trioxide and antimony pentoxide since these are more stable and commercially available.

Mixtures of different alkanolamines and/or different hydrocarboxylic acids may be used in the preparation of the product.

The products of the invention are prepared by reacting together the alkanolamine, the hydroxycarboxylic acid and the antimony oxide. The order of addition of reactants to the reaction is not critical, however it is usually more convenient to first combine the alkanolamine and the hydroxycarboxylic acid and then form the final product by reacting the antimony oxide with the intermediate product. Alternatively all three reactants may be simultaneously combined. If the alkanolamine and/or the hydroxycarboxylic acid are liquid in their natural state at the reaction conditions the reaction may be carried out without the use of a solvent or diluent. However, it is usually preferable to use an inert diluent or solvent as the reaction vehicle. Suitable solvents are those in which the hydrocarboxylic acid is soluble. In general, the hydroxycarboxylic acid is soluble in polar solvents, such as, water, alcohols, formamides, etc. The preferred solvent is water because it is inexpensive and does not introduce additional organic compounds into the units being treated.

The alkanolamine and hydroxycarboxylic acid reactants readily combine to form an intermediate salt product. This reaction usually occurs at ambient temperatures, although it is sometimes preferred to heat the reactants to increase the rate of dissolution of reactants and the rate of the reaction. In the case of the reaction between the intermediate salt and the antimony oxide, it's usually necessary to employ elevated temperatures. Any temperature less than the decomposition temperature of the products or reactants can be used. The reaction used in the manufacture of the final product is generally carried out at temperatures in the range of about 30° to 300° C. and preferably at temperatures in the range of about 50° to 200° C. The reactions of the invention can be carried out at any desired pressure.

The ratio of reactants is not critical and is usually determined by economics. If the reaction is carried out at reactant ratios other than stoichiometric it is preferred that the alkanolamine or the hydrocarboxylic acid be used in excess because antimony oxides are insoluble in water and are more expensive than the other reactants. Of course, the stoichiometric ratio of the reactants will vary depending upon the products formed. When polyfunctional carboxylic acids and polyfunctional alkanolamines are used it is possible that more than one chemical compound will be formed. In general, about 1 to 10 and preferably about 2 to 6 moles of alkanolamine and about 1 to 10 and preferably about 2 to 6 moles of hydroxycarboxylic acid are used for each mole of antimony oxide.

In a typical procedure for preparing the products of the invention the selected alkanolamine is combined with an aqueous solution of the selected hydroxycarboxylic acid and the mixture is stirred, with or without heating, until a clear solution is formed. The antimony oxide is then added to the alkanolamine-hydroxycarboxylic acid solution and this mixture is heated with continuous agitation until all of the antimony oxide is dissolved, thereby forming the end product. The product may be used as is or it may be dried and used as a solid product.

Other substances, such as other cracking catalyst metal poison passivators or corrosion inhibitors may be added to the finished product, if desired.

The following examples illustrate specific embodiments of the invention. Unless otherwise specified, parts and percentages are on a weight basis.

EXAMPLE 1

Reaction of Tartaric Acid, Antimony Trioxide and Monoethanolamine

To a clean reaction flask fitted with a reflux condensor was added 332 gm. of distilled water. Agitation was started and 404 gm. (2.7 moles) of tartaric acid was added. 165 gm. (2.7 mole) of monoethanolamine was then charged to the reactor and an exotherm to 75° C. occurred. The pH of this solution was about 4. After mixing for 15 minutes 374 gm. (1.28 moles) of antimony trioxide was charged to the reactor. The antimony trioxide dispersed through the solution producing a mixture having a thick milky appearance. The mixture was heated to reflux (100° C.) and held at that temperature for 9 hours. At the end of this time the solution had cleared to a light brown liquid. This product was analyzed and found to contain 20% by weight of antimony as Sb metal.

A sample of this compound was heated to 150° C. to drive off water. The residue was a clear brown solid. This solid was readily soluble in water at room temperature, but was not soluble in xylene, isopropyl alcohol, trichloromethane or ethylene glycol.

EXAMPLE 2

Reaction of Lactic Acid, Antimony Trioxide and Monoethanolamine

To a clean reaction flask fitted with a reflux condenser were charged 27 gm. (0.3 moles) of lactic acid and 18 gm. (0.3 moles) of monoethanolamine. The solution was mixed thoroughly and cooled to room temperature so that the pH of the solution could be determined. The pH was reported to be 8.6 and with the addition of another 47 gm. lactic acid the pH was lowered to 4.0. While the solution was being stirred, 18 gm. of distilled water was added to the reactor, followed by 14.5 gm. (0.05 moles) of antimony trioxide. The resulting mixture had a milky appearance. The mixture was heated to reflux and held at that temperature for 3 hours. At the end of this time the solution had cleared to a yellow liquid. The resulting product contained 11% by weight of antimony as Sb metal.

EXAMPLE 3

Reaction of Glycolic Acid, Antimony Trioxide and Monoethanolamine.

To a clean reactor fitted with a reflux condenser were charged 17.9 gm. (0.165 moles) of a 70% aqueous glycolic acid solution and 9.2 gm. (0.15 moles) of monoethanolamine At this point the pH was determined to be 5.2. Another 13.5 gm. of glycolic acid solution was added to lower the pH to 3.7. As the mixture was stirred, 38 gm. As the mixture was stirred, 38 gm. of distilled water and 7.3 gm. (0.025 moles) of antimony trioxide were charged to the reactor. The solution had a milky white appearance. The mixture was heated to reflux and held at reflux for 7.5 hours. At the end of this time the solution had become a clear brown liquid. This product had an antimony content of 7.1% by weight as antimony metal.

EXAMPLE 4

Reaction of Tartaric Acid, Antimony Pentoxide and Monoethanolamine

The procedure of Example 1 was repeated except that the reactants and charge weights were 227 gms of distilled water, 150 gms (1.0 mole) of tartaric acid, 61 gms (1.0 mole) of monoethanolamine and 158 gms (0.49 mole) of antimony pentoxide. The final product was a light brown liquid which was readily soluble in water.

The foregoing examples illustrate various embodiments of the invention using different hydroxycarboxylic acids. As indicated in each example the antimony oxide was completely reacted. Example 1 showed that a solid product which was readily soluble in water was obtained.

Although the invention has been described with reference to specific examples, it is understood that variations of these are comtemplated. The scope of the invention is limited only by the breadth of the appended claims.

What is claimed is:

1. A method of preparing water-soluble antimony compounds comprising:
   (a) reacting an alkanolamine with a hydroxycarboxylic acid and
   (b) reacting the product of (a) with an antimony oxide at an elevated temperature.

2. A method of preparing water-soluble compounds of antimony comprising:
   (a) reacting (1) a nitrogen-containing compound having the structure

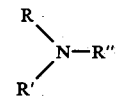

wherein R and R' are each independently hydrogen, an alkyl group having 1 to 10 carbon atoms or a hydroxyalkyl group having 1 to 10 carbon atoms and R" is a hydroxyalkyl group having 1 to 10 carbon atoms and the total number of carbon atoms in R, R' and R" is 1 to about 12, with (2) a hydroxycarboxylic acid having up to 12 total carbon atoms and containing 1 to 4 carboxyl groups and 1 to 4 hydroxyl groups, and wherein at least one of said hydroxyl groups is in the alpha position relative to a carboxyl group, and
   (b) reacting the product obtained in step (a) with an antimony oxide selected from antimony trioxide, antimony pentoxide and mixtures of these at a temperature in the range of about 30° to 300° C.

3. The process of claim 2 wherein R and R' each have 0 to about 4 carbon atoms, R" has 2 to 4 carbon atoms and the total number of carbon atoms in R, R' and R" is 2 to about 10.

4. The process of claim 2 wherein the hydroxycarboxylic acid contains 1 to 4 carboxyl groups, 1 to 4 hydroxyl groups and a maximum of about 8 carbon atoms.

5. The process of claim 4 wherein the hydroxycarboxylic acid is selected from glycolic acid, tartaric acid, citric acid, lactic acid, malic acid and mixtures of these.

6. The process of claim 4 wherein the alkanolamine has 2 to about 6 carbon atoms.

7. The process of claim 6 wherein the alkanolamine is selected from ethanolamine, propanolamine, butanolamine and mixtures of these.

8. The process of claim 7 wherein the antimony oxide is antimony trioxide.

9. A product prepared by the process of any one of claims 2 to 8.